(12) United States Patent
Melkent (10) Patent No.: US 8,414,628 B2
(45) Date of Patent: Apr. 9, 2013

(54) BONE SCREW

(75) Inventor: Anthony J. Melkent, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 990 days.

(21) Appl. No.: 11/586,915

(22) Filed: Oct. 26, 2006

(65) Prior Publication Data

US 2008/0177335 A1    Jul. 24, 2008

(51) Int. Cl.
*A61B 17/04* (2006.01)
*A61B 17/86* (2006.01)
*A61F 2/08* (2006.01)

(52) U.S. Cl.
USPC ............... 606/309; 606/300; 606/264

(58) Field of Classification Search ............ 606/246, 606/264, 265–268, 270, 272, 328, 277–279, 606/295, 300–321; 411/387.1
See application file for complete search history.

(56) References Cited

U.S. PATENT DOCUMENTS

| | | | |
|---|---|---|---|
| 4,963,144 A | 10/1990 | Huene | |
| 5,573,537 A | 11/1996 | Rogozinski | |
| 6,059,785 A | 5/2000 | Schavan et al. | |
| 6,306,140 B1 * | 10/2001 | Siddiqui | 606/315 |
| 6,368,319 B1 | 4/2002 | Schaefer | |
| 6,402,752 B2 | 6/2002 | Schaffler-Wachter et al. | |
| 6,623,227 B2 * | 9/2003 | Scott et al. | 411/387.6 |
| 6,855,105 B2 | 2/2005 | Jackson, III | |
| 6,988,859 B2 | 1/2006 | Borschert et al. | |
| 7,087,057 B2 | 8/2006 | Konieczynski et al. | |
| 2001/0004694 A1 | 6/2001 | Carchidi et al. | |
| 2001/0021852 A1 | 9/2001 | Chappius | |
| 2004/0044345 A1 | 3/2004 | DeMoss et al. | |
| 2005/0038438 A1 * | 2/2005 | Anderson et al. | 606/73 |
| 2005/0228379 A1 | 10/2005 | Jackson | |
| 2006/0036248 A1 * | 2/2006 | Ferrante et al. | 606/64 |
| 2006/0036252 A1 | 2/2006 | Baynham et al. | |
| 2006/0084979 A1 | 4/2006 | Jackson | |
| 2006/0100621 A1 | 5/2006 | Jackson | |
| 2006/0100622 A1 | 5/2006 | Jackson | |
| 2006/0106383 A1 | 5/2006 | Biedermann et al. | |

(Continued)

FOREIGN PATENT DOCUMENTS

EP    0699420    10/2002
GB    2369867    6/2002

(Continued)

OTHER PUBLICATIONS

International Search Report and Written Opinion of the International Searching Authority issued in corresponding PCT Application.

*Primary Examiner* — Pedro Philogene
*Assistant Examiner* — Christina Negrellirodriguez (57) ABSTRACT

A bone screw and method of inserting a bone screw into a bone is disclosed. In one example, the bone screw includes a tip segment for creating a starter hole in the bone. A pilot segment is located proximally of the tip segment for creating a pilot hole in the bone after creation of the starter hole. A threaded segment is located proximally of the pilot segment for fixedly securing the bone screw in the bone. A head is located proximally of the threaded segment for allowing a surgical rod to be fixedly secured to the bone screw.

20 Claims, 8 Drawing Sheets

U.S. PATENT DOCUMENTS

| | | |
|---|---|---|
| 2006/0122612 A1* | 6/2006 | Justin et al. .................. 606/73 |
| 2006/0135960 A1 | 6/2006 | Munro et al. |
| 2006/0149232 A1 | 7/2006 | Sasing |
| 2006/0149263 A1 | 7/2006 | Newcomb et al. |
| 2006/0200133 A1 | 9/2006 | Jackson |
| 2006/0241594 A1* | 10/2006 | McCarthy et al. ............ 606/61 |
| 2007/0134072 A1* | 6/2007 | Su ............................ 411/387.1 |

FOREIGN PATENT DOCUMENTS

| | | |
|---|---|---|
| WO | WO 98/30167 | 7/1998 |
| WO | WO 98/31293 | 7/1998 |
| WO | WO 99/00065 | 1/1999 |

* cited by examiner

BONE SCREW

TECHNICAL FIELD

The present invention relates generally to bone screws, and more particularly to a bone screw that does not require preparation of a bone or bone segment prior to insertion into the bone.

BACKGROUND

Bone screws have been used in spinal instrumentation since at least as early as the 1960s. A bone screw is a screw that is usually made of titanium and perhaps finished with inert titanium nitride (gold colored finish). If a bone screw is used in a pedicle of the spine, then it is called a pedicle screw. Pedicle screws are most often used as part of a system of screws, plates and rods that immobilize part of the spine. During anterior fixation or plating of cervical vertebral bodies, the spine is approached from an anterior or anterlo-lateral direction and bone screws are typically used to solidly mount a spinal plate to the affected vertebrae. This helps spinal fusion wherein two or more vertebrae are encouraged to grow together after damage to the intervening disks or spinal fracture makes the original structure unstable.

Current pedicle screws require multiple steps in order to implant the screw in the pedicle. Typically, these steps include creating a starting hole with a very small drill bit, pedicle or bone probe, or awl. Once the starter hole is created, a bigger drill bit or pedicle probe may be used to create a pilot hole. After the pilot hole has been created, the pilot hole may then be tapped in a size compatible with the threads of the pedicle screw using a tap. Some pedicle screws are self-tapping thereby eliminating the step of tapping the pilot hole. Some bone screws, not pedicle screws, include a drill-bit feature associated with a thread and shaft. Each additional step required during a surgical procedure requiring the use of bone screws creates a greater potential for the patient to experience complications from the procedure as well as the chances for a physician to make a mistake due to fatigue during long constructs requiring numerous bone screws.

Thus, there remains a need for improved, inexpensive, and easy to use bone screws and methods for inserting bone screws in bone that minimize the need for preparatory steps prior to insertion of the bone screws into the bone.

SUMMARY

A bone screw is disclosed that is capable of directly being inserted into a bone without the requirement of separately creating a starter hole, a pilot hole and tapping the pilot hole. In one embodiment, the bone screw includes a distal tip segment, an intermediate pilot segment, an intermediate threaded segment, and a proximal head or fixation segment. The distal tip segment is used to create a starter hole in the bone. The intermediate pilot segment is used to create a pilot hole in the bone and the intermediate threaded segment is used to fixedly secure the bone screw into the bone. In alternative embodiments, the distal tip segment and the intermediate pilot segment may be combined into a pilot segment which, in essence, eliminates the starter hole segment. This embodiment may be useful for procedures in which a starter hole is not necessary, is being placed in the bone by another instrument, or where paddle probes are used as the tip segment.

The fixation segment is used as an anchor for a rod or the like that is utilized as part of an immobilization system for a spine. In one embodiment, the fixation segment comprises a head that has a U-shaped format. In other embodiments, the fixation segment may comprise a straight shaft that is clamped onto by other devices. It is envisioned that the bone screw disclosed herein may be used for other types of surgical procedures beyond spinal procedures such as, implant or replacement procedures for example, and as such, may include other head configurations.

The tip segment of the bone screw comprises a conical shaped portion that includes a cutout that forms a cutting edge in the tip segment. In another embodiment, the tip segment comprises an awl or a probe. As set forth above, the tip segment is used to create a starter or small hole in the bone prior to creation of a pilot hole. The pilot segment comprises an elongate shaft that includes a flute running up the elongate shaft. The flute may be a straight flute or a spiral flute. The elongate shaft may be tapered such that it increases in size as the pilot segment enters the bone, but in other embodiments it may not be tapered. The flute includes a cutting edge for removing bone to create the pilot hole for the bone screw. The pilot segment may be formed like a drill bit for the purposes of removing bone.

The threaded segment is used to fixedly secure the bone screw in place in the bone. The threaded segment includes a thread that is used to secure the bone screw in the bone. In one embodiment, the thread is formed as a self-tapping thread so that the pilot hole does not need to be tapped. In another embodiment, the threaded segment includes a self-tapping feature as well as threads. The self-tapping features taps the pilot hole prior to the threads of the threaded segment being inserted into the threads created in the bone by the self-tapping feature. The head of the bone screw may be a conventional type screw head, but in one embodiment, comprises a U-shaped head designed to receive a rod of an implant. As such, the bone screw disclosed herein is capable of providing three functions that include creating a starter hole, creating a pilot hole, and creating a threaded connection that fixedly secures the bone screw in the bone. This eliminates the need for a surgeon to perform three separate steps in order to insert a bone screw into a bone.

In another embodiment, a bone screw is disclosed that includes a drill bit segment located at a distal end of the bone screw. The drill bit segment is used to create a pilot hole in the bone. A threaded segment is located proximate the drill bit segment for fixedly securing the bone screw in the bone. The threaded segment may include a self-tapping feature that taps the pilot hole created by the drill bit segment prior to entry of the threads of the threaded segment. A head may be located proximate the threaded segment which may comprise a conventional head or a U-shaped head designed to receive a rod.

In yet another embodiment, a bone screw is disclosed that includes a probe segment located at a distal end of the bone screw. The probe segment is used to create a pilot hole in the bone. A threaded segment is located proximate the drill bit segment for fixedly securing the bone screw in the bone. The threaded segment may include a self-tapping feature that taps the pilot hole created by the drill bit segment prior to entry of the threads of the threaded segment. A head located proximate the threaded segment may comprise a conventional head or a U-shaped head designed to receive a rod.

Another aspect includes a method of inserting a bone screw into a bone. In this embodiment, a starter hole is formed in the bone with a tip segment of the bone screw. Once the starter hole is formed, a pilot hole is formed in the bone with a pilot segment of the bone screw. Finally, a threaded connection in the bone is formed with a threaded segment of the bone screw proximate the pilot segment such that the bone screw is fixedly secured in the bone.

Another method for inserting a bone screw in a bone involves the use of a drill bit segment or a probe segment. The drill bit or probe segment, depending on which embodiment is used, is used to form a pilot hole in the bone. The bone screw includes a threaded segment that is used to create a threaded connection between the bone and the bone screw once the pilot hole is formed.

Other systems, methods, features and advantages of the invention will be, or will become apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The components in the figures are not necessarily to scale, emphasis instead being placed upon illustrating the principles of the invention. Moreover, in the figures, like reference numerals designate corresponding parts throughout the different views.

FIG. 11a illustrates a portion of a bone screw having a curved paddle probe tip segment.

FIG. 11b is a side view of a portion of the curved paddle probe tip segment illustrated in FIG. 11a.

DETAILED DESCRIPTION

Referring collectively to FIGS. 1-4, a representative bone screw 10 is illustrated that extends along a longitudinal axis and includes a distal tip segment 12, an intermediate pilot segment 14, an intermediate threaded segment 16, and a proximal fixation segment 18. As used herein, distal refers to the direction toward which the bone screw 10 is advanced as the bone screw 10 is engaged to bone and proximal refers to the direction opposite the distal direction. The tip segment 12 is used to create a small starter hole 20 or to enlarge an existing starter hole 20 in a bone 22, which in one example comprises a pedicle, in which the bone screw 10 is to be inserted. In this embodiment, the tip segment 12 includes a blunt tip 24 and a conical portion 26 that includes a cutout 28 defining a cutting edge 30 that gradually increases in size or diameter as it runs up the conical portion 26 toward the pilot segment 14. As such, using the bone screw 10 disclosed herein eliminates the need to create a starter hole with a separate instrument and as a separate step during a surgical procedure.

As set forth in greater detail below, in one embodiment of the present invention, the bone screw 10 is operable to create a starter hole, to create a pilot hole, and to fixedly secure the bone screw 10 in a bone of a patient with threads. This saves the surgeon time and shortens the length of surgical procedures involving placement of multiple bone screws 10. As a result, the patient does not have to spend as much time undergoing a surgical procedure and the stress experienced by physicians during long procedures is reduced. In other embodiments, creation of a starter hole may not be necessary and as such, only a pilot segment 14 may be included in these embodiments of the bone screw 10. In these embodiments, the tip segment 12 and the pilot segment 14 may be viewed as one and the same.

The tip segment 12 transitions into a pilot segment 14 that is located proximate to the tip segment 12. The pilot segment 12 is used to create a pilot hole 32 in the bone 22 after the starter hole 20 has been formed by the tip segment 12 or by a separate instrument. The pilot segment 12 includes an elongate cylindrical portion 34 that includes a straight flute 36 traversing upwardly a predetermined distance of the elongate cylindrical portion 34. The straight flute 36 includes a cutting edge 38 for cutting the pilot hole 32 in the bone 22. The cylindrical portion 34 may slightly increase in diameter or be tapered as it approaches the threaded segment 16. As such, the pilot segment 14 is operable to form a pilot hole 32 in the bone 22. This eliminates the need for a surgeon to utilize a second instrument to create a pilot hole 32 after the starter hole 20 has been created in the bone 22, which eliminates a surgical step.

The pilot segment 14 transitions into a threaded segment 16 that is located proximate to the pilot segment 14. The threaded segment 16 is used to fixedly secure the bone screw 10 in the bone 22. The threaded segment 16 has a helically wound, radially outwardly extending bone implantable thread 40 axially extending from the end of the pilot segment 14 to approximately the fixation segment 18. The threaded segment 16 may also include a self-tapping feature 42 located at the transition point between the pilot segment 14 and the threaded segment 16. The self-tapping feature 42 cuts a thread in the inside surface of the pilot hole 32 so that the threads 40 of the threaded segment 16 engage or mate with the threads cut in the pilot hole 32. In alternative embodiments, the threads 40 may comprise self-tapping threads 40 thereby eliminating the need for the self-tapping feature 42 to be included in the threaded segment 16.

As set forth above, the threaded segment 16 transitions into a fixation segment 18 that is located proximate to the pilot segment 14. In one embodiment, the fixation segment 18 comprises a U-shaped head that includes a pair of opposed upwardly standing arms 44 that extend upwardly from a cylindrical base 46 to a top surface 48. The arms 44 form a U-shaped cradle 50 and define a U-shaped channel 52 between the arms 44. The U-shaped cradle 50 has substantially the same radius of rods used in spinal procedures for operably snugly receiving the rod, such as rod 11 shown in dashed lines in FIG. 4.

Each of the arms 44 has an interior surface 54 that defines a cylindrical profile. The interior surface 54 of each of the arms 44 includes an inner threaded member 56 located distally of the top surface 48 and running about half way down the arms 44. Although the inner threaded member 56 is illustrated as a helical thread, it is also envisioned that a buttress thread, a square thread, a reverse angle thread or other thread-like structures could be used. A locking member or set screw 58 is included for securing the rod in the U-shaped cradle 50. The locking member 58 screws into the inner threaded member 56 to apply pressure or force to the rod 11 thereby ensuring that the rod 11 is fixed in place.

Although the fixation segment 18 is illustrated as a U-shaped head throughout the figures, it should be appreciated that the term fixation segment should be broadly construed to include other types of fixation mechanisms. For example, the fixation segment 18 may comprise an elongate shaft (e.g. shaft 102 of FIG. 7) in some embodiments of the present invention. A clamping device of another surgical device or simply a clamping device may be used to clamp onto the elongate shaft. In other embodiments of the present invention, the bone screw 10 may take the form of a cannulated screw.

Figure 5:
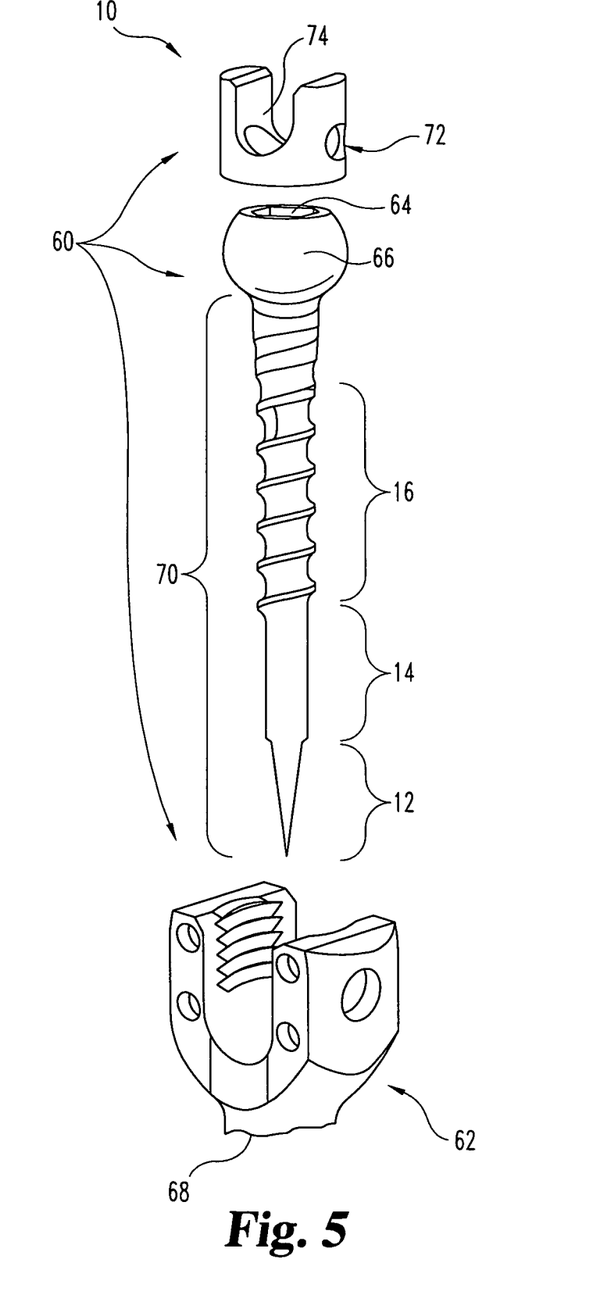
FIG. 5 illustrates a bone screw having a polyaxial head assembly.

Referring to FIG. 5, in yet another embodiment, the bone screw 10 includes a polyaxial head assembly 60. In this embodiment, a U-shaped head 62 is included whereby the threaded segment 16, the pilot segment 14, and the starter segment 12 are provided with free angular and pivoting movement with respect to the U-shaped head 62. A female socket portion 64 may be formed in a spherical head 66 of the bone screw 10 for applying torque to the threaded segment 16, the pilot segment 14, and the starter segment 12 to position them in the bone 22. The spherical head 66 is positioned proximate the threaded segment 16.

The U-shaped head 62 is generally configured the same as in the previous embodiment of the present invention except that it includes an axial opening 68 to permit passage of a shank portion 70 of the bone screw 10 there through while maintaining the spherical head 66 therein. A compression cap 72, which is adapted to be positioned within the U-shaped head 62, has a generally cylindrical shape and includes a rod-receiving surface 74. The bone screw 10 disclosed herein is provided in one embodiment with a polyaxial head assembly 60 that allows the shank portion 70 of the bone screw 10 to have free or selective angular movement with respect to the U-shaped head 62. The polyaxial head assembly 60 set forth in FIG. 5 should be viewed in an illustrative sense as several different types of polyaxial head assemblies exist that may be utilized in the present invention.

Figure 6:
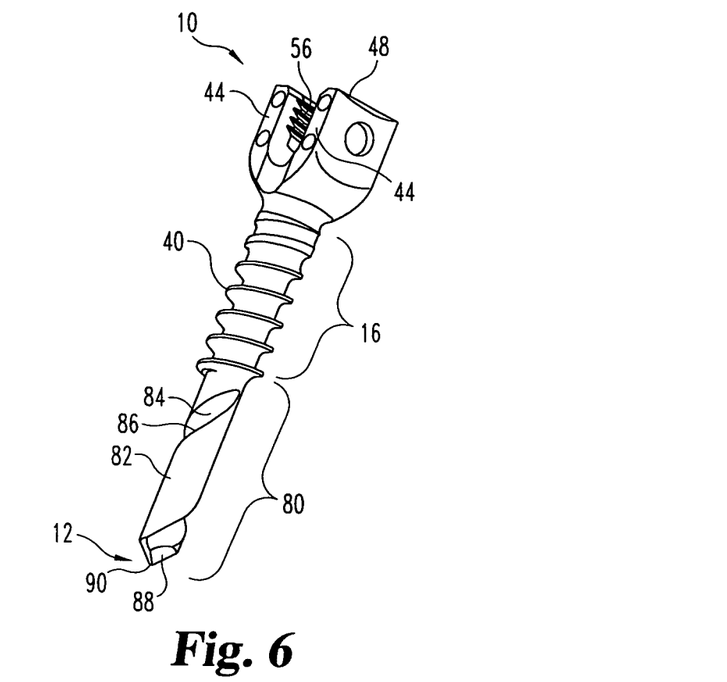
FIG. 6 illustrates a bone screw having a drill bit type segment.

Referring to FIG. 6, in another embodiment, the bone screw 10 may include a starter segment 12 that transitions into a drill bit segment 80. The drill bit segment 80 includes an elongate cylindrical portion 82 that includes a spiral flute 84 that runs in a spiral configuration up the elongate cylindrical portion 82 a predetermined distance to approximately the beginning of the threaded segment 16. The spiral flute 84 includes a cutting edge 86 for removing bone when the bone screw 10 is installed in a bone 22. The drill bit segment 80 is used to create a pilot hole for the threaded segment 16. The starter segment 12 includes a conical shaped portion 88 that terminates at a sharp point 90. Those skilled in the art should recognize that the style, shape and size of the flutes may vary in alternative embodiments of the present invention.

Figure 7:
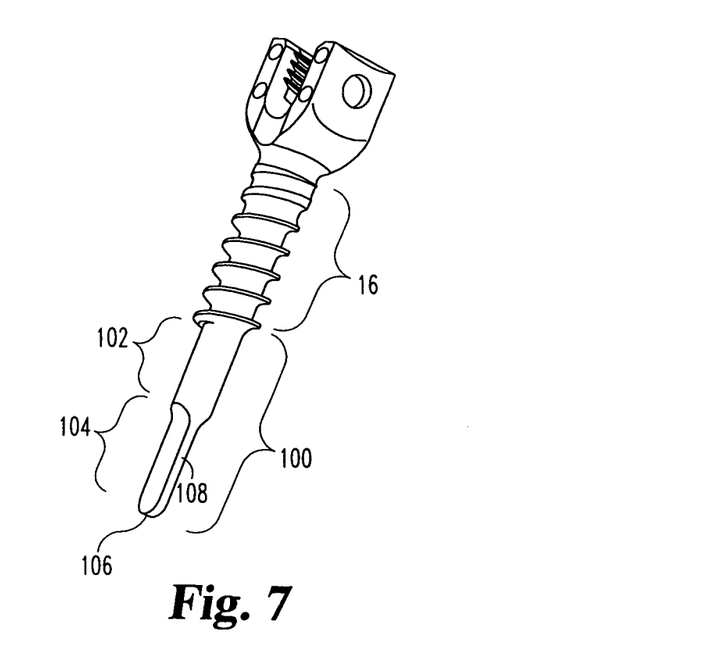
FIG. 7 illustrates a bone screw having a probe segment.

Referring to FIG. 7, in this embodiment, the bone screw 10 includes a pedicle probe segment 100 that transitions into the threaded segment 16. The pedicle probe segment 100 includes an elongate shaft portion 102 and a probe portion 104. The probe portion 104 illustrated in FIG. 7 is a paddle probe having a tip 106 and a paddle portion 108. The probe portion 104 may be selected from several different types of probes such as a Lenke style probe, a paddle style probe, and a curette style probe to name a few. As illustrated in FIG. 5, the starter segment 12 may also be shaped in the form of an awl having a sharp tip.

Figure 8:
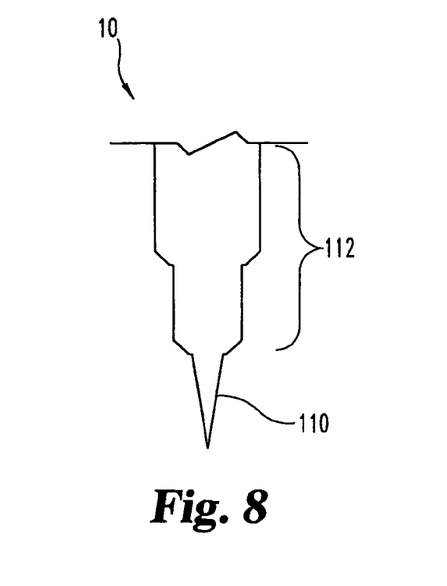
FIG. 8 illustrates a portion of a bone screw having an awl tip and a probe portion.

Referring to FIG. 8, a portion of a bone screw 10 is illustrated that includes an awl tip 110 that transitions into a probe segment 112. The awl tip 110 is used to create a starter hole in the bone 22 and the probe segment 112 is used to create a pilot hole in the bone 22. The awl tip 110 comprises a spike sharpened to a fine point that is capable of cutting through bone 22. The probe segment 112 is similar to the probes described with respect to the previous embodiments of the present invention and may comprise, for example, a paddle probe. The bone screw 10 illustrated in FIG. 8 includes a threaded segment 16 and a head 18 as set forth in FIGS. 1-4.

Figure 1:
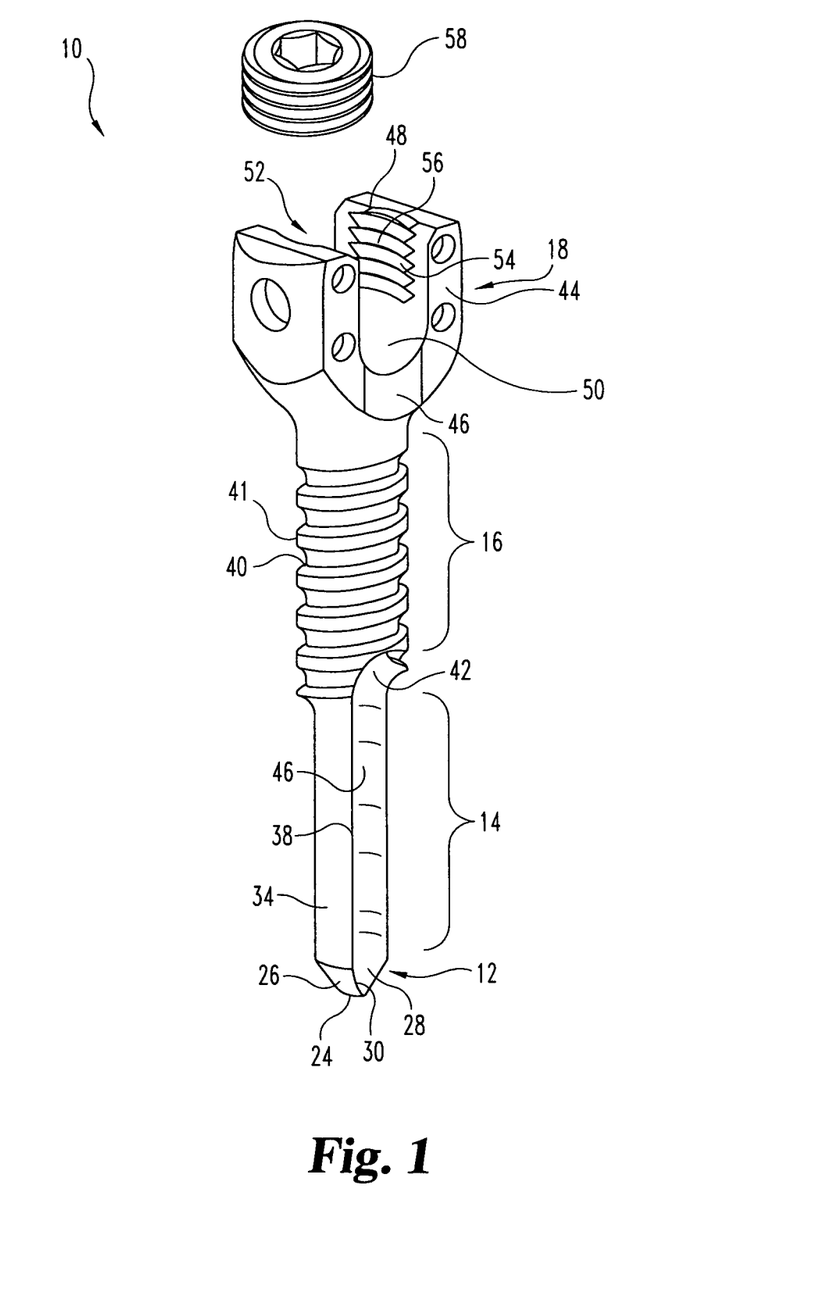
FIG. 1 is a perspective view of a representative bone screw.
Figure 2:
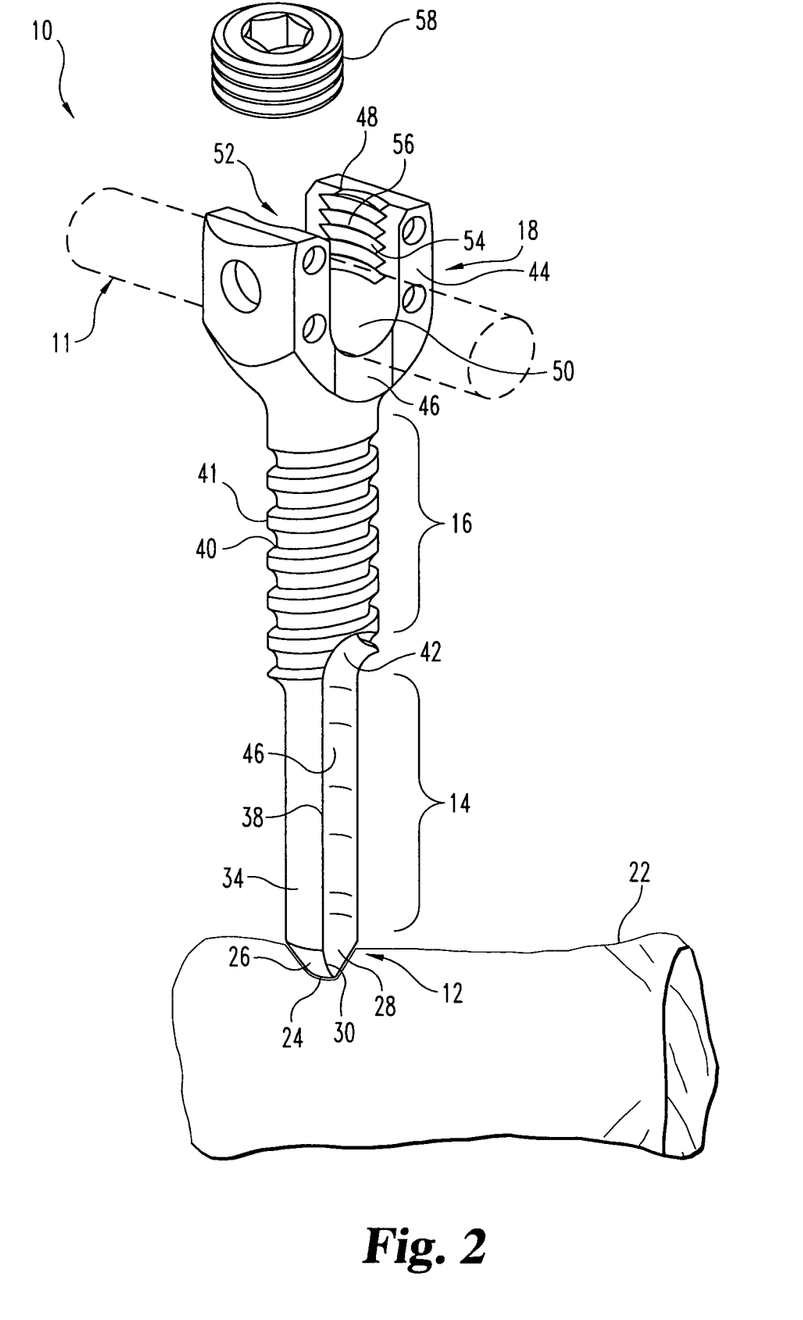
FIG. 2 illustrates the bone screw of FIG. 1 making a starter hole in a pedicle of a spine.
Figure 3:
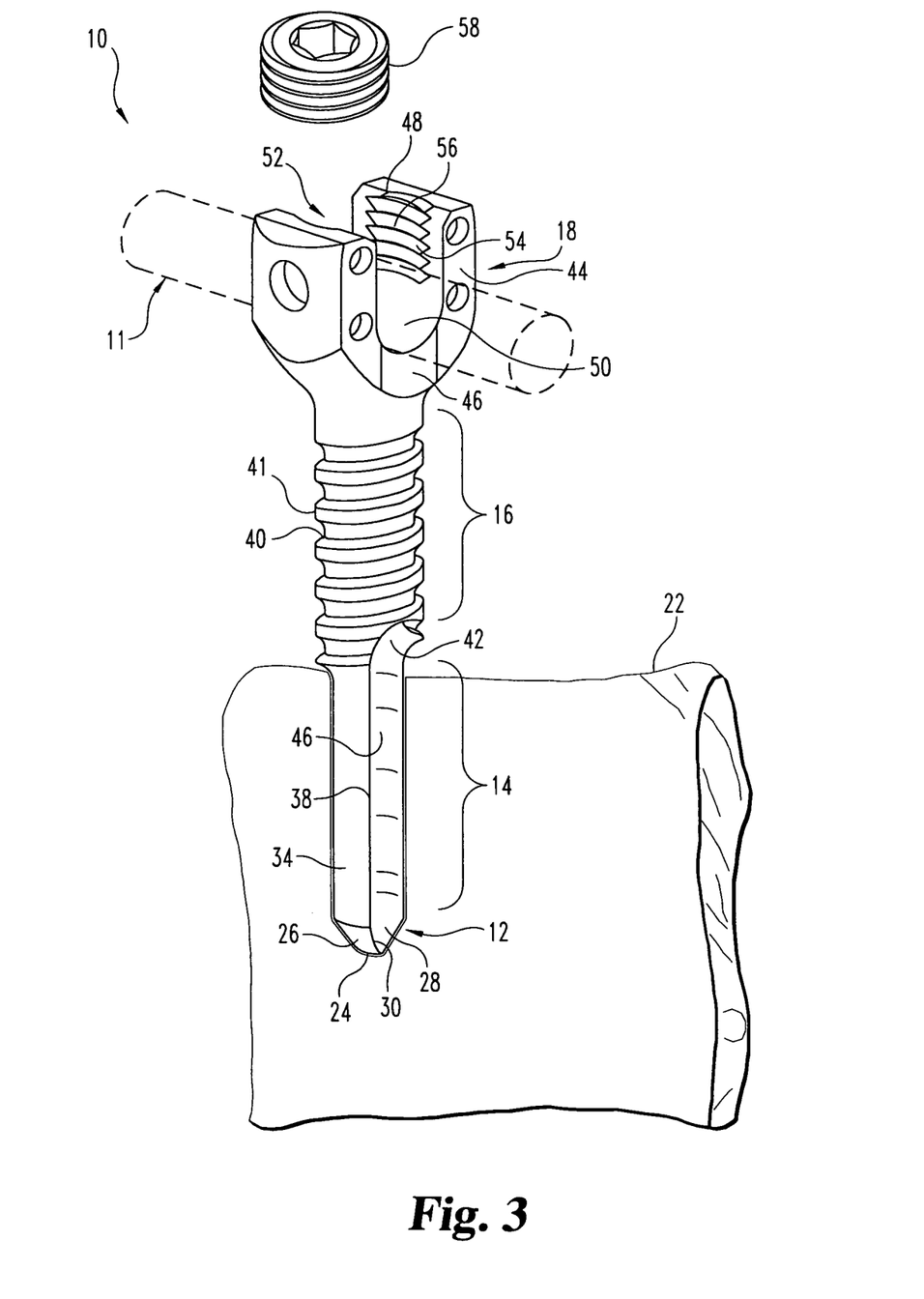
FIG. 3 illustrates the bone screw of FIG. 1 making a pilot hole in the pedicle.
Figure 4:
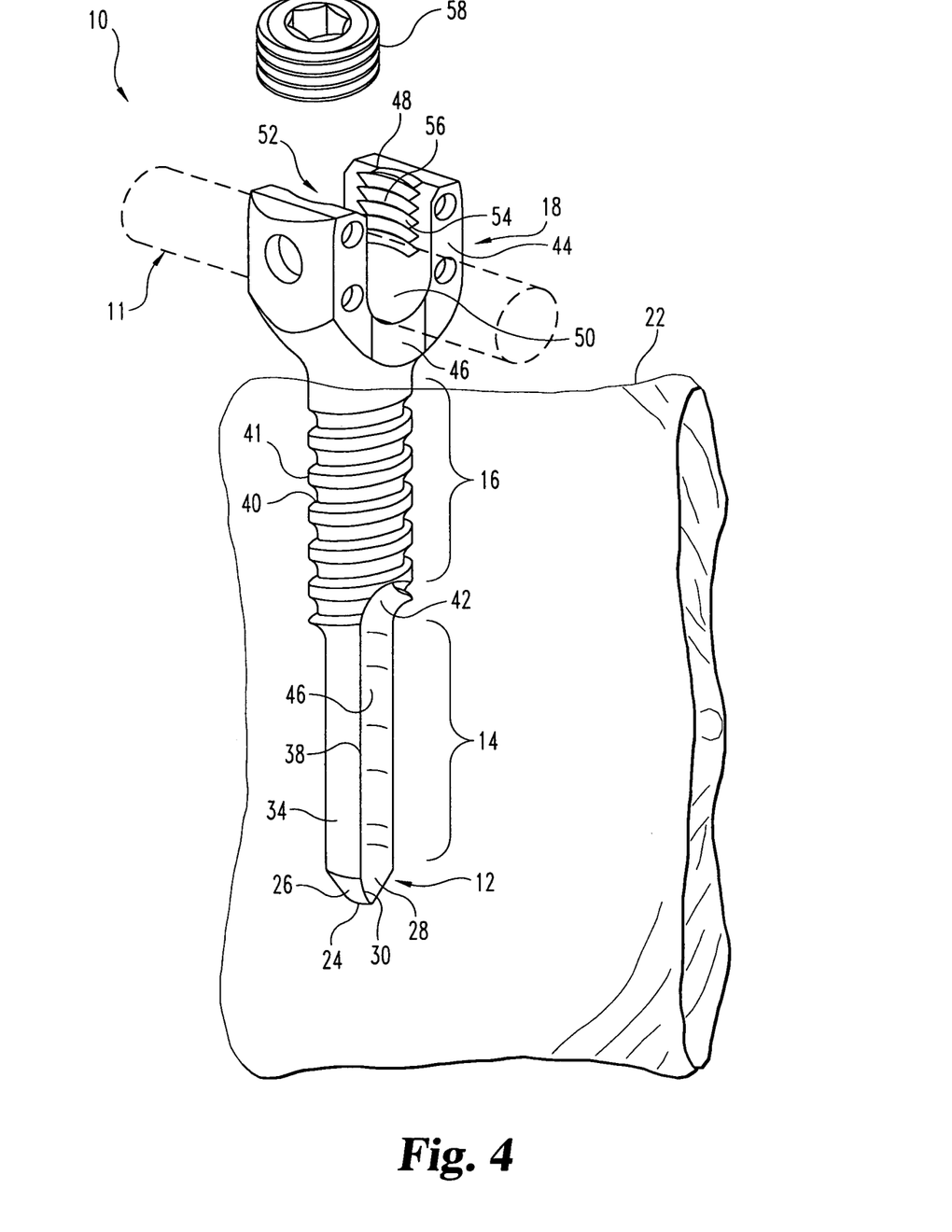
FIG. 4 illustrates the bone screw of FIG. 1 being threaded in to the pedicle.

Referring to FIGS. 2-4, another aspect of the present invention relates to a method of inserting a bone screw 10 into a bone 22. In one embodiment, the method comprises the steps of (a) forming a starter hole 20 with a tip segment 12 of the bone screw 10; (b) forming a pilot hole 32 with a pilot segment 14 of the bone screw 10 proximate the tip segment 12; and (c) forming a threaded connection 41 in the bone 22 with a threaded segment 16 of the bone screw 10 proximate the pilot segment 14 such that the bone screw 10 is fixedly secured in the bone 22.

Yet another embodiment includes a method of inserting a bone screw 10 in a bone 22, comprising the steps of (a) forming a pilot hole 32 with a drill bit segment 80 (see FIG. 6) of the bone screw 10; and (b) forming a threaded connection 41 in the bone 22 with a threaded segment 16 of the bone screw 10 proximate the drill bit segment 80 such that the bone screw 10 is fixedly secured in the bone 22.

In yet another embodiment, a third method of inserting a bone screw 10 in a bone 22 comprises the steps of (a) forming a pilot hole 32 with a probe segment 100 (see FIG. 7) of the bone screw 10; and (b) forming a threaded connection 41 in the bone with a threaded segment 16 of the bone screw 10 proximate the probe segment 100 such that the bone screw 10 is fixedly secured in the bone 22. The surgical methods also include engaging an implant to the bone screw 10. In one embodiment, a spinal rod 11 is positioned in and engaged in the head 18 with a locking member, such as set screw 58.

Figure 9:
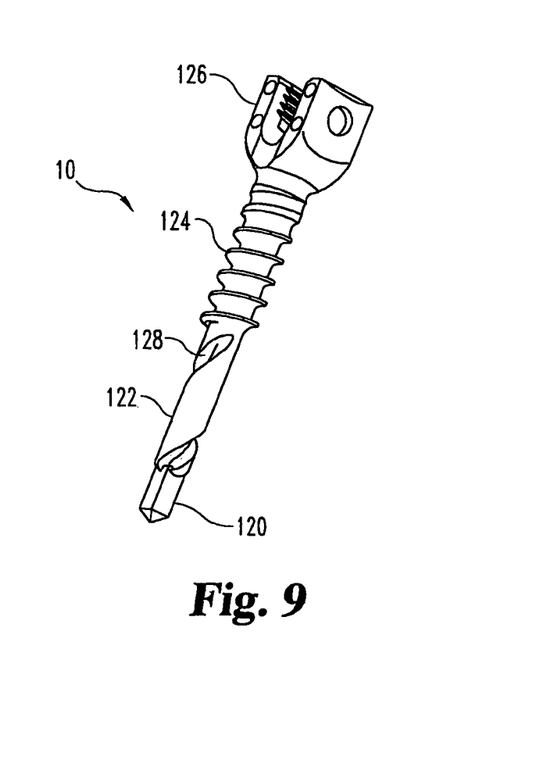
FIG. 9 illustrates a portion of a bone screw having a square-shaped tip segment.

Referring to FIG. 9, yet another embodiment of the present invention discloses a bone screw 10 that includes a square-shaped awl tip segment 120. The square-shaped awl tip segment 120 transitions into a drill bit segment 122. The drill bit segment 122 transitions into a threaded segment 124 that is connected with a head segment 126. The square-shaped awl tip segment 120 is used to create a starter hole. The drill bit segment 122 is used to create a pilot hole and includes at least one flute 128. Although illustrated as a spiral flute, the flute 128 may also comprise a straight flute. In addition, the threaded segment 124 may also include a self-tapping feature as previously set forth.

Figure 10:
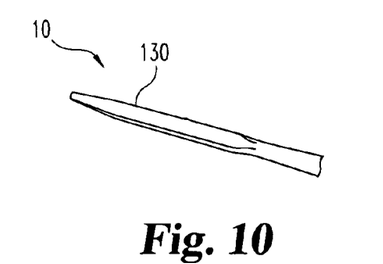
FIG. 10 illustrates a portion of a bone screw having a Lenke style tip segment.
Figures 11A, 11B:
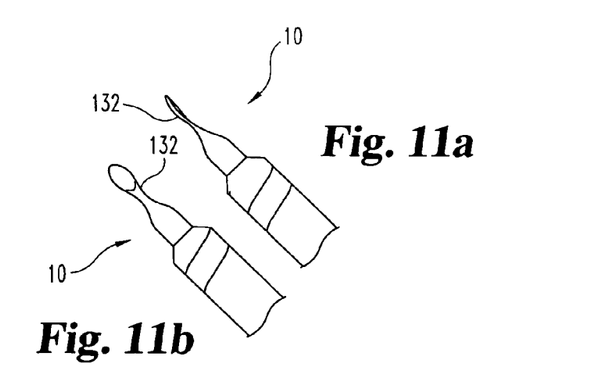
Figure 12:
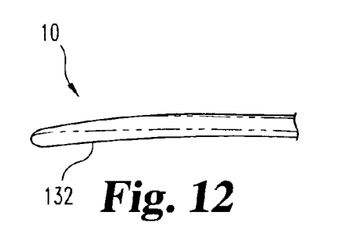
FIG. 12 illustrates a portion of a bone screw having another curved paddle probe tip segment.
Figure 13:
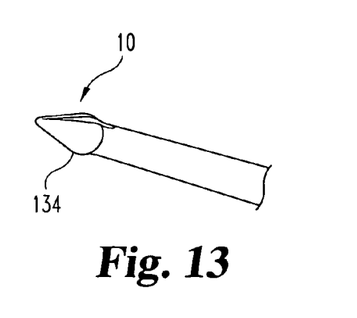
FIG. 13 illustrates a portion of a bone screw having a acorn tip segment.
Figure 14:
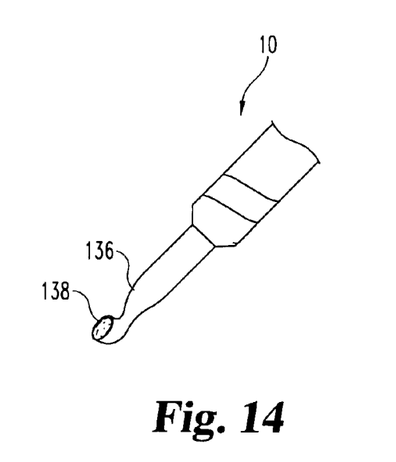
FIG. 14 illustrates a portion of a bone screw having a cup curette tip segment.

Referring to FIG. 10, a representative Lenke style tip segment 130 is illustrated that may be utilized on the tip segment 12 of the bone screw 10. Referring to FIGS. 11a and 11b, a curved paddle probe 132, also known as a "Steffe Style probe," that may be utilized on the tip segment 12 of the bone screw is illustrated. The curved paddle probe 132 includes a curved section that is connected with the intermediate pilot segment 14. FIG. 12 illustrates another version of a curved paddle probe 132. As illustrated in FIG. 13, an acorn style tip segment 134 may also be utilized to start the starter hole. FIG. 14 illustrates a cup curette style tip segment 136 that includes a cup 138 located at the very end of the tip segment 12.

While the invention has been illustrated and described in detail in the drawings and foregoing description, the same is to be considered as illustrative and not restrictive in character.

What is claimed is:

1. A bone screw, comprising:
   a tip segment having a conical portion and a cutout in said conical portion defining a first cutting edge, wherein said tip segment is used to create a starter hole in a bone;
   a pilot segment proximate said tip segment for creating a pilot hole in said bone after creation of said starter hole, wherein said pilot segment includes a cylindrical portion and a straight flute defined in said cylindrical portion having a second cutting edge, wherein said straight flute lies along a same vertical axis as said cutout in said tip segment and said first cutting edge transitions into said second cutting edge;
   a threaded segment defining a longitudinal axis and disposed proximate said pilot segment for fixedly securing said bone screw in said bone;
   a fixation segment proximate said threaded segment, the fixation segment comprising a U-shaped head configured to receive a rod of an implant, the U-shaped head including a spherical base integral with said threaded segment and a pair of opposed upstanding arms, each arm extending upwardly from the spherical base to a top surface, each arm further including an inner threaded member located distally of the top surface and extending substantially half the distance of the arm; and
   a locking member for securing the rod in the U-shaped head by screwing into the inner threaded member to apply pressure to the rod thereby fixing the rod in place,
   wherein the straight flute extends parallel to the longitudinal axis of the threaded segment, and said tip segment has an outer surface behind said cutout and said first cutting edge that is continuous with an outer surface of said pilot segment and is free of gaps or recesses.

2. The bone screw of claim 1, wherein said tip segment includes an awl.

3. The bone screw of claim 1, wherein said threaded segment includes a self-tapping feature located at a point where said pilot segment transitions into said threaded segment.

4. The bone screw of claim 1, wherein said fixation segment comprises an elongate shaft.

5. The bone screw of claim 1, wherein said pilot segment has a maximum diameter that is equivalent to a maximum diameter of said threaded segment.

6. The bone screw of claim 1, wherein a first portion of said bone screw includes said cutout and said straight flute and a second portion of said bone screw opposite said first portion has an even outer surface that is free of any gaps or recesses.

7. The bone screw of claim 1, wherein said pilot segment has a concave outer surface opposite said straight flute that is free of any gaps or recesses.

8. The bone screw of claim 1, wherein the first cutting edge gradually increases in diameter as it runs up said conical portion toward said pilot segment.

9. The bone screw of claim 1, wherein the cylindrical portion is tapered between a first end adjacent said threaded segment and a second end adjacent said tip segment.

10. The bone screw of claim 1, wherein the tip segment includes a blunt tip.

11. The bone screw of claim 1, wherein the threaded segment includes an outer surface including self-tapping threads.

12. The bone screw of claim 1, wherein the bone screw is cannulated.

13. A method of inserting a bone screw in a vertebral body, comprising:
   forming a starter hole in a pedicle of said vertebral body with a tip segment of said bone screw, wherein said tip segment includes a conical portion and a cutout that defines a first cutting edge;
   forming a pilot hole with a pilot segment of said bone screw proximate said tip segment, wherein said pilot segment includes an elongate tapered cylindrical portion including a straight flute traversing upwardly a predetermined distance of the elongate cylindrical portion, the straight flute defining a second cutting edge in substantially the same vertical plane as the first cutting edge, wherein said first cutting edge transitions to said second cutting edge above a distal end of said tip segment, and said cutout transitions to said straight flute, said tip segment having an outer surface behind said cutout and said first cutting edge that is continuous with an outer surface of said pilot segment and is free of gaps or recesses; and
   forming a threaded connection in said pedicle with a threaded segment of said bone screw defining a longitudinal axis and disposed proximate said pilot segment such that said bone screw is fixedly secured in said vertebral body, wherein the straight flute extends parallel to the longitudinal axis of the threaded segment.

14. The method of claim 13, wherein said tip segment comprises an awl.

15. The method of claim 13, wherein said threaded segment includes a self-tapping feature located at a point where said pilot segment transitions into said threaded segment.

16. A bone screw, comprising:
   a pilot segment for creating a pilot hole in said bone after creation of a starter hole, wherein said pilot segment includes a cylindrical portion and a straight flute defined in said cylindrical portion having a first cutting edge, said pilot segment having an outer surface behind said straight flute that is free of any gaps or recesses;
   a threaded segment defining a longitudinal axis and disposed proximate said pilot segment for fixedly securing said bone screw in said bone;
   a fixation segment proximate said threaded segment, the fixation segment;
   comprising a U-shaped head configured to receive a rod of an implant, the U-shaped head including a spherical base integral with said threaded segment and a pair of opposed upstanding arms, each arm extending upwardly from the spherical base to a top surface, each arm further including an inner threaded member located distally of the top surface and extending substantially half the distance of the arm;
   a locking member for securing the rod in the U-shaped head by screwing into the inner threaded member to apply pressure to the rod thereby fixing the rod in place; and
   a tip segment at a distal end of said pilot segment for creating a said starter hole in a bone, wherein said tip segment includes a conical portion and a cutout defining a second cutting edge;
   wherein said second cutting edge of said tip segment transitions to said first cutting edge, wherein said cutout and said straight flute share a common vertical axis, wherein the straight flute extends parallel to the longitudinal axis of the threaded segment and wherein said cutout transitions to said straight flute along said common vertical axis.

17. The bone screw of claim 16, further comprising a self-tapping feature positioned at a transition point between said pilot segment and said threaded segment.

18. The bone screw of claim 17, wherein said tip segment includes a blunt tip.

19. The bone screw of claim 16, wherein the bone screw is a polyaxial screw.

20. The bone screw of claim 16, wherein the threaded segment includes a spherical head and the U-shaped head includes an axial opening configured to permit passage of the pilot segment and the threaded segment therethrough such that the spherical head is disposed in the axial opening and the fixation segment is pivotable relative to the pilot segment and the threaded segment through a plurality of axes.

\* \* \* \* \*